(12) United States Patent
Rodgers et al.

(10) Patent No.: US 9,101,491 B2
(45) Date of Patent: Aug. 11, 2015

(54) SPINAL SURGICAL IMPLANT AND RELATED METHODS

(75) Inventors: W. Blake Rodgers, Jefferson City, MO (US); Matthew Curran, Carlsbad, CA (US); Benjamin Arnold, San Diego, CA (US)

(73) Assignee: NuVasive, Inc., San Diego, CA (US)

( * ) Notice: Subject to any disclaimer, the term of this patent is extended or adjusted under 35 U.S.C. 154(b) by 0 days.

(21) Appl. No.: 12/317,867

(22) Filed: Dec. 29, 2008

(65) Prior Publication Data

US 2011/0125266 A1     May 26, 2011

Related U.S. Application Data

(60) Provisional application No. 61/009,546, filed on Dec. 28, 7.

(51) Int. Cl.
*A61F 2/44*     (2006.01)
*A61F 2/46*     (2006.01)
(Continued)

(52) U.S. Cl.
CPC ............... *A61F 2/4611* (2013.01); *A61F 2/447* (2013.01); *A61F 2002/2835* (2013.01); *A61F 2002/305* (2013.01); *A61F 2002/3008* (2013.01); *A61F 2002/30462* (2013.01); *A61F 2002/30466* (2013.01); *A61F 2002/30492* (2013.01); *A61F 2002/30507* (2013.01); *A61F 2002/30565* (2013.01); *A61F 2002/30624* (2013.01); *A61F 2002/30629* (2013.01); *A61F 2002/30637* (2013.01); *A61F 2002/30777* (2013.01); *A61F 2002/30779* (2013.01); *A61F 2002/30784* (2013.01); *A61F 2002/30785* (2013.01); *A61F 2002/30841* (2013.01); *A61F 2002/30879* (2013.01); *A61F 2002/30904* (2013.01); *A61F 2002/30967* (2013.01); *A61F 2002/448* (2013.01); *A61F 2002/4415* (2013.01); *A61F 2002/4475* (2013.01); *A61F 2002/4485* (2013.01); *A61F 2002/4628* (2013.01); *A61F 2310/00023* (2013.01); *A61F 2310/00179* (2013.01)

(58) Field of Classification Search
CPC ............................. A61B 2/4611; A61B 2/447
USPC ............................. 606/279; 623/17.11–17.16
See application file for complete search history.

(56) References Cited

U.S. PATENT DOCUMENTS 3,848,601 A    11/1974   Ma et al.
3,867,728 A     2/1975   Stubstad et al.
(Continued)

FOREIGN PATENT DOCUMENTS

EP     0716840    6/1996
EP     0880938    2/1998
(Continued)

*Primary Examiner* — Ellen C Hammond
(74) *Attorney, Agent, or Firm* — Jonathan Spangler; Jennifer Russell

(57) ABSTRACT

An intervertebral implant consisting of multiple elements connected by a flexible member and a method of positioning said implant via an operative corridor having an axis oblique to the disc plane. The implant is advanced through the operative corridor by altering the orientation of the first element of the implant such that it is in general alignment with the disc space plane without altering the alignment of the second element of the implant. Upon insertion of the first element into the disc space, the orientation of the second element is altered to be in general alignment with the disc space and the second element is inserted into the disc space.

8 Claims, 7 Drawing Sheets

(51) Int. Cl.
  *A61F 2/28* (2006.01)
  *A61F 2/30* (2006.01)

(56) References Cited

U.S. PATENT DOCUMENTS

| | | | |
|---|---|---|---|
| 4,501,269 A | 2/1985 | Bagby | |
| 4,657,550 A | 4/1987 | Daher | |
| 4,743,256 A | 5/1988 | Brantigan | |
| 4,781,591 A | 11/1988 | Allen | |
| 4,834,757 A | 5/1989 | Brantigan | |
| 4,878,915 A | 11/1989 | Brantigan | |
| 4,932,975 A | 6/1990 | Main et al. | |
| 4,961,740 A | 10/1990 | Ray et al. | |
| 5,015,247 A | 5/1991 | Michelson | |
| 5,026,373 A | 6/1991 | Ray et al. | |
| 5,047,055 A | 9/1991 | Bao et al. | |
| 5,055,104 A | 10/1991 | Ray | |
| 5,071,437 A | 12/1991 | Steffee | |
| 5,171,278 A | 12/1992 | Pisharodi | |
| 5,263,953 A | 11/1993 | Bagby | |
| 5,290,494 A | 3/1994 | Coombes et al. | |
| 5,306,307 A | 4/1994 | Senter et al. | |
| 5,306,309 A | 4/1994 | Wagner et al. | |
| 5,364,400 A | 11/1994 | Rego, Jr. et al. | |
| 5,397,364 A | 3/1995 | Kozak | |
| 5,405,391 A | 4/1995 | Henderson et al. | |
| 5,413,602 A | 5/1995 | Metz-Stavenhagen | |
| 5,425,772 A | 6/1995 | Brantigan | |
| 5,431,658 A | 7/1995 | Moskovich | |
| 5,443,514 A | 8/1995 | Steffee | |
| 5,443,515 A | 8/1995 | Cohen et al. | |
| 5,454,811 A | 10/1995 | Huebner | |
| 5,458,638 A | 10/1995 | Kuslich et al. | |
| 5,484,437 A | 1/1996 | Michelson | |
| 5,489,307 A | 2/1996 | Kuslich et al. | |
| 5,489,308 A | 2/1996 | Kuslich et al. | |
| 5,514,180 A | 5/1996 | Heggeness et al. | |
| 5,522,899 A | 6/1996 | Michelson | |
| 5,534,030 A | 7/1996 | Navarro et al. | |
| 5,540,688 A | 7/1996 | Navas | |
| 5,562,736 A | 10/1996 | Ray et al. | |
| 5,571,190 A | 11/1996 | Ulrich | |
| 5,571,192 A | 11/1996 | Schonhoffer | |
| 5,593,409 A | 1/1997 | Michelson | |
| 5,609,636 A | 3/1997 | Kohrs et al. | |
| 5,611,800 A | 3/1997 | Davis et al. | |
| 5,632,747 A | 5/1997 | Scarborough et al. | |
| 5,645,598 A | 7/1997 | Brosnahan et al. | |
| 5,653,761 A | 8/1997 | Pisharodi | |
| 5,653,762 A | 8/1997 | Pisharodi | |
| 5,665,122 A | 9/1997 | Kambin | |
| 5,669,909 A | 9/1997 | Zdeblick et al. | |
| 5,676,703 A | 10/1997 | Gelbard | |
| 5,683,394 A | 11/1997 | Rinner | |
| 5,683,464 A | 11/1997 | Wagner et al. | |
| 5,700,264 A | 12/1997 | Zucherman et al. | |
| 5,700,291 A | 12/1997 | Kuslich et al. | |
| 5,700,292 A | 12/1997 | Margulies | |
| 5,702,449 A | 12/1997 | McKay | |
| 5,702,451 A | 12/1997 | Biedermann et al. | |
| 5,702,453 A | 12/1997 | Rabbe et al. | |
| 5,702,454 A | 12/1997 | Baumgartner | |
| 5,702,455 A | 12/1997 | Saggar | |
| 5,716,415 A | 2/1998 | Steffee | |
| 5,728,159 A | 3/1998 | Stroever et al. | |
| 5,741,253 A | 4/1998 | Michelson | |
| 5,741,261 A | 4/1998 | Moskovitz et al. | |
| 5,766,252 A | 6/1998 | Henry et al. | |
| 5,772,661 A | 6/1998 | Michelson | |
| 5,782,830 A | 7/1998 | Farris | |
| 5,782,832 A | 7/1998 | Larsen et al. | |
| 5,785,710 A | 7/1998 | Michelson | |
| 5,797,909 A | 8/1998 | Michelson | |
| 5,800,550 A | 9/1998 | Sertich | |
| 5,814,084 A | 9/1998 | Grivas et al. | |
| 5,860,973 A | 1/1999 | Michelson | |
| 5,865,845 A | 2/1999 | Thalgott | |
| 5,865,848 A | 2/1999 | Baker | |
| 5,885,299 A | 3/1999 | Winslow et al. | |
| 5,888,224 A | 3/1999 | Beckers et al. | |
| 5,904,719 A | 5/1999 | Errico et al. | |
| 5,910,315 A | 6/1999 | Stevenson et al. | |
| 5,968,098 A | 10/1999 | Winslow | |
| 6,004,326 A | 12/1999 | Castro et al. | |
| 6,008,433 A | 12/1999 | Stone | |
| 6,015,436 A | 1/2000 | Schunhuffer | |
| 6,039,761 A | 3/2000 | Li et al. | |
| 6,042,582 A | 3/2000 | Ray | |
| 6,045,580 A | 4/2000 | Scarborough et al. | |
| 6,048,342 A | 4/2000 | Zucherman et al. | |
| 6,059,829 A | 5/2000 | Schlapfer et al. | |
| 6,063,088 A | 5/2000 | Winslow | |
| 6,083,225 A | 7/2000 | Winslow et al. | |
| 6,110,210 A * | 8/2000 | Norton et al. | 623/17.16 |
| 6,120,503 A | 9/2000 | Michelson | |
| 6,120,506 A | 9/2000 | Kohrs et al. | |
| 6,143,033 A | 11/2000 | Paul et al. | |
| 6,159,211 A | 12/2000 | Boriani et al. | |
| 6,159,215 A | 12/2000 | Urbahns et al. | |
| 6,193,756 B1 | 2/2001 | Studer et al. | |
| 6,200,347 B1 | 3/2001 | Anderson | |
| 6,224,607 B1 | 5/2001 | Michelson | |
| 6,224,631 B1 | 5/2001 | Kohrs | |
| 6,235,059 B1 | 5/2001 | Benezech et al. | |
| 6,241,769 B1 | 6/2001 | Nicholson et al. | |
| 6,241,771 B1 | 6/2001 | Gresser et al. | |
| 6,251,140 B1 | 6/2001 | Marino et al. | |
| 6,258,125 B1 | 7/2001 | Paul et al. | |
| 6,277,149 B1 | 8/2001 | Boyle et al. | |
| 6,319,257 B1 | 11/2001 | Carignan et al. | |
| 6,371,989 B1 | 4/2002 | Chauvin et al. | |
| 6,383,221 B1 | 5/2002 | Scarborough et al. | |
| 6,387,130 B1 * | 5/2002 | Stone et al. | 623/17.16 |
| 6,409,766 B1 | 6/2002 | Brett | |
| 6,432,140 B1 | 8/2002 | Lin | |
| 6,440,142 B1 | 8/2002 | Ralph et al. | |
| 6,442,814 B1 | 9/2002 | Landry et al. | |
| 6,454,806 B1 | 9/2002 | Cohen et al. | |
| 6,468,311 B2 | 10/2002 | Boyd et al. | |
| 6,485,518 B1 | 11/2002 | Cornwall et al. | |
| 6,503,279 B1 | 1/2003 | Webb et al. | |
| 6,527,773 B1 | 3/2003 | Lin et al. | |
| 6,595,998 B2 | 7/2003 | Johnson et al. | |
| 6,626,905 B1 | 9/2003 | Schmiel et al. | |
| 6,635,086 B2 | 10/2003 | Lin | |
| 6,648,895 B2 | 11/2003 | Burkus et al. | |
| 6,676,703 B2 | 1/2004 | Biscup | |
| 6,706,067 B2 | 3/2004 | Shimp et al. | |
| 6,743,255 B2 | 6/2004 | Ferree | |
| 6,746,454 B2 | 6/2004 | Winterbottom et al. | |
| 6,746,484 B1 | 6/2004 | Liu et al. | |
| 6,755,841 B2 | 6/2004 | Fraser et al. | |
| 6,824,564 B2 | 11/2004 | Crozet | |
| 6,851,430 B2 * | 2/2005 | Tsou | 128/898 |
| 6,855,167 B2 | 2/2005 | Shimp et al. | |
| 6,964,687 B1 | 11/2005 | Bernard et al. | |
| 6,979,353 B2 | 12/2005 | Bresina | |
| 6,984,245 B2 | 1/2006 | McGahan et al. | |
| 6,986,788 B2 | 1/2006 | Paul et al. | |
| 6,989,031 B2 | 1/2006 | Michelson | |
| 7,018,416 B2 | 3/2006 | Hanson et al. | |
| 7,125,425 B2 | 10/2006 | Foley et al. | |
| 7,192,447 B2 | 3/2007 | Rhoda | |
| 7,244,258 B2 | 7/2007 | Burkus et al. | |
| 7,303,583 B1 | 12/2007 | Schaer et al. | |
| 7,326,251 B2 | 2/2008 | McCombe et al. | |
| 7,776,095 B2 * | 8/2010 | Peterman et al. | 623/17.16 |
| 7,867,277 B1 | 1/2011 | Tohmeh | |
| 7,951,203 B2 | 5/2011 | McCombe et al. | |
| 8,016,829 B2 * | 9/2011 | Mahoney et al. | 606/86 A |
| 8,021,430 B2 | 9/2011 | Michelson | |
| 8,187,334 B2 | 5/2012 | Curran et al. | |
| 8,246,686 B1 | 8/2012 | Curran et al. | |
| 8,251,997 B2 | 8/2012 | Michelson | |

(56) References Cited

U.S. PATENT DOCUMENTS

| | | |
|---|---|---|
| 8,361,156 B2 | 1/2013 | Curran et al. |
| 8,506,636 B2 | 8/2013 | Dye |
| 8,574,301 B2 | 11/2013 | Curran et al. |
| 8,579,909 B2 | 11/2013 | Burkus et al. |
| 8,591,589 B2 | 11/2013 | McCombe et al. |
| 8,608,804 B2 | 12/2013 | Curran et al. |
| 2007/0162138 A1* | 7/2007 | Heinz ........................ 623/17.16 |
| 2008/0058933 A1* | 3/2008 | Garner et al. .............. 623/17.11 |

FOREIGN PATENT DOCUMENTS

| | | |
|---|---|---|
| WO | WO 94/04100 | 3/1994 |
| WO | WO 95/01810 | 1/1995 |
| WO | WO 96/08205 | 3/1996 |
| WO | WO 97/33525 | 9/1997 |
| WO | WO 98/17208 | 4/1998 |

* cited by examiner

SPINAL SURGICAL IMPLANT AND RELATED METHODS

CROSS-REFERENCE TO RELATED APPLICATIONS

This non-provisional application claims the benefit of the filing date under 35 USC 119(e) to the commonly owned U.S. Provisional Patent Application Ser. No. 61/009,546, entitled "Spinal Surgical Implant and Relted Methods," and filed on Dec. 28, 2007, the entire contents of which are incorporated by reference as if set forth herein in its entirety.

BACKGROUND OF THE INVENTION

I. Field of the Invention

This invention relates generally to spine surgery and, in particular, to a surgical implant for separating adjacent spinal vertebrae.

II. Discussion of the Prior Art

The spinal column is made up of individual vertebrae that provide support for the body and allow spinal movement. Between each vertebra sits a fibrocartilaginous disc that serves as a cushion and allows slight movement of the vertebrae. Spinal fusion procedures are common surgical techniques used to correct problems with displaced, damaged, or degenerated discs due to trauma, disease, or aging. Currently estimates suggest there are approximately 500,000 to 750,000 spinal fusion procedures performed each year in the United States. Generally, spinal fusion procedures involve removing the diseased or damaged disc and inserting one or more intervertebral implants into the resulting disc space. Introducing the intervertebral implant restores the height between adjacent vertebrae, which reduces or eliminates neural impingement and pain commonly associated with a damaged or diseased disc.

While various intervertebral implants are currently available in the prior art, there exists a need for an implant that can be inserted when surgical angles are less than optimal due to surgical constraints, the anatomical location of the vertebrae, or when two or more fusions are performed within one surgical corridor. When the surgical angle is less than optimal, the advancing implant may gouge or injure the vertebral endplate as it enters the intervertebral space. Also, it may be necessary for the surgeon to remove a portion of the side of the vertebral body to improve the entry angle into the intervertebral space. This may have the undesirable effect of destabilizing the interbody fusion. The present invention addresses this need.

SUMMARY OF THE INVENTION

The present invention includes a spinal fusion system for performing spinal fusion between adjacent lumbar vertebrae, including an exemplary spinal fusion implant. In one embodiment, the implant has a generally rectangular shape, with a leading element, a trailing element. The leading element and the trailing element are connected via flexible element. The flexible element allows the trailing element to move relative to the leading element (or vice versa). Thus, trailing element (and/or leading element) may bend from a neutral position in which the trailing element (and/or leading element) is aligned with the longitudinal axis L to a biased position in which the trailing element (and/or the leading element) deviates from the longitudinal axis L. This flexibility allows the implant to adopt various temporary profiles that may be desirable, particularly during insertion. For example, when the operative corridor used to access the disc space is offset or angled relative to the plane of the disc space the implant may transition from the offset access trajectory to the disc space in stages (e.g. the leading element may transition before the trailing element), thus protecting the vertebral endplates during insertion. The flexible element should thus be flexible enough to allow the trailing element to bend appropriately without effecting the overall integrity and strength of the implant.

The flexible element may comprise any number of suitable forms including, but not limited to a spring, a textile body, and an elastomeric body. The leading element, trailing element, and flexible element may be formed of a single component. Alternatively, leading element, trailing element, and flexible element may comprise separate components. It will be appreciated that any manner of mechanisms or techniques may be used attach the flexible element to the leading element and trailing element. By way of example only, the flexible element may be attached via mechanical fasteners (e.g. snaps, rivets, screws, pins, etc . . . ), chemical bonding, thermal bonding, adhesives, and molding.

The implant is preferably configured for lateral introduction into the disc space. By way of example, the implant may be particularly advantageous for implanting positioning the implant at L5-S1 via a lateral approach. By way of example only, the operative corridor may be created using any know tissue distraction and/or tissue retraction systems. The skin entry position depends upon individual patient anatomy but should be positioned just superior to the iliac crest. The distal end of the tissue distraction/retraction system may then be advanced at an angle towards the L5-S1 disc space, avoiding the iliac crest and thereafter opened to a final working corridor. After the creation of the operative corridor, the intervertebral space may be prepared via any number of well known preparation tools, including but not limited to kerrisons, rongeurs, pituitaries, and rasps. According to one embodiment, the preparation tools may utilize distal working ends angularly offset from the longitudinal axis of the tool shafts to facilitate entry into the disc space through the angled operative corridor. After preparation is complete, the implant is preferably advanced through the operative corridor in the neutral position (i.e. with leading element and trailing element aligned with the longitudinal axis L and the operative corridor).

The flexible element permits the trailing element to move relative to the leading element as the leading element enters the disc space. In this manner, the longitudinal axis L of the implant is permitted to rotate into alignment with the disc space, despite the small height of the disc space relative to the length of the implant and any space constraints in the operative corridor and the implant may be advanced into the disc space without causing damage.

According to another embodiment the leading element and trailing element are connected by an articulating element. The articulating element allows the trailing element to move relative to the leading element (or vice versa). The articulating element may be constructed of any suitable biocompatible material, but preferably, comprises the same material as leading element and trailing element. One articulating element preferably attaches to an interior surface of both sidewalls on each side of the implant. By attaching the articulating element to the interior surface of sidewalls the outer dimensions of implant may remain the same. Any number of additional articulation elements within one implant is also contemplated. Intervening members may connect the articulating elements with the leading and trailing ends. The additional articulation elements allow the implant to advance into an intervertebral space at greater and greater angles, depending on the number of articulation elements.

In still other embodiments, the leading element and trailing element may be connected via wires or tethers. Additional one or more additional element may be situated between the leading element and the trailing element. Various mechanisms for locking the elements together after insertion are also contemplated.

BRIEF DESCRIPTION OF THE DRAWINGS

The invention will be more fully understood from the following detailed descriptions taken in conjunction with the accompanying drawings, in which.

DESCRIPTION OF THE PREFERRED EMBODIMENT

Illustrative embodiments of the invention are described below for the purposes of understanding the principles of the invention. No limitation of the scope of the invention is therefore intended. In the interest of clarity, not all features of an actual implementation are described in this specification. It will be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure. The invention disclosed herein boasts a variety of inventive features and components that warrant patent protection, both individually and in combination.

Figure 1:
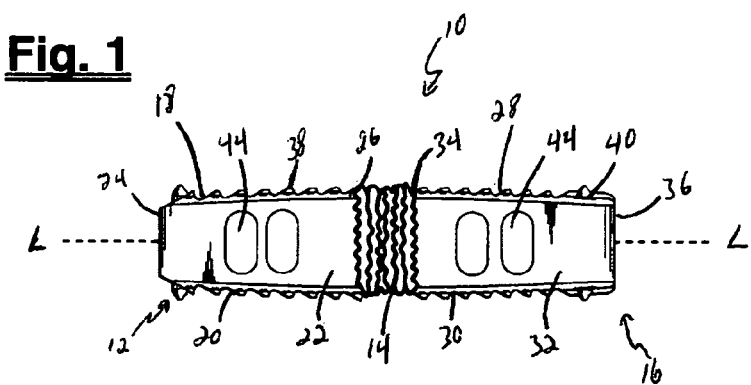
FIG. 1 is a side view of an implant having a first element and a second element movably connected about the longitudinal axis, according to one embodiment of the present invention.
Figure 2:
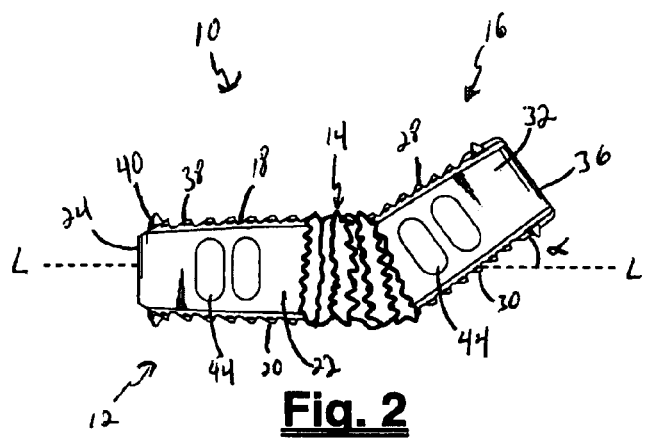
FIG. 2 is a side view of the implant of FIG. 1 wherein an element of the implant is offset relative to the longitudinal axis, according to one embodiment of the present invention.
Figure 3:
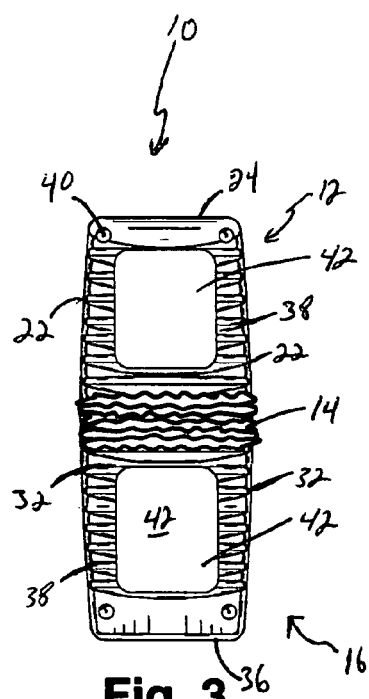
FIG. 3 is a top view of the implant of FIG. 1, according to one embodiment of the present invention.

With reference to FIG. 1-3, there is shown an example embodiment of an implant 10 for positioning within the intervertebral disc space between adjacent vertebral bodies of a spine. The implant 10, when deposited in the disc space, facilitates spinal fusion and alleviates pain by restoring the disc space to a desired height while natural bone growth occurs through and/or past the implant 10. Over time the bone growth results in the formation of a boney bridge between the adjacent vertebral bodies. The implant 10 is particularly adapted for introduction into the disc space via a lateral (trans-psoas) approach to the spine. The implant may nevertheless be introduced through any of a variety of other approaches (depending on the implant size), including posterior, anterior, antero-lateral, and postero-lateral approaches, without departing from the scope of the present invention. The implant 10 includes a longitudinal axis L, a leading element 12, a trailing element 16, and a flexible element 14 extending along the longitudinal axis L. The flexible element 14 is situated between the leading element 12 and trailing element 16 along the longitudinal axis L and connects the leading element 12 with the trailing element 16.

The implant 10 may be provided in any number of sizes by varying one or more of the implant height, width, and length. By way of example only, the implant may be provided with a length dimension ranging from 30 mm to 60 mm. By way of further example, the implant may be provided with a width dimension ranging from 15 mm to 22 mm. By way of still further example, the implant may be provided with a height dimension ranging from 5 mm to 20 mm. The size ranges described, by way of example only, are generally appropriate for implantation into the lumbar region of the spine. The dimensions of the implant may be altered according to proportions of the particular patient. Further variation of the implant dimensions may be implemented to produce implants generally appropriate for implantation into either of the thoracic spine and the cervical spine.

The leading element 12 and trailing element 16 may be of bone or non-bone construction. By way of example, the leading element 12 and trailing element 16 may be cut and shaped from a suitable allograft bone. Preferably, the allograft source comprises a donor femur, however, it will be appreciated that any suitable bone may be used. Alternatively, the leading element 12 and trailing element 16 may be comprised of any suitable bio-compatible material including, but not limited to, polymer compositions (e.g. poly-ether-ether-ketone (PEEK) and/or poly-ether-ketone-ketone (PEKK) or any combination of PEEK and PEKK), and metals (e.g. titanium).

The leading element 12 has a top surface 18, a bottom surface 20, opposing sidewalls 22 (which comprise an anterior side and a posterior side when the implant is positioned in the disc space), a distal end 24, and a proximal end 26. The trailing element 16 has a top surface 28, a bottom surface 30, opposing sidewalls 32 (which comprise an anterior side and a posterior side when the implant is positioned in the disc space), a distal end 34, and a proximal end 36. Though not shown, it will be appreciated that the opposing side walls 22, 32 may be dimensioned with differing heights in order to promote the natural curvature of the spine. That is, by way of example, the sidewalls 22, 32 may be dimensioned such that the sidewalls comprising the anterior side when the implant is positioned in the disc space have a greater height than the sidewalls comprising the posterior side, thus restoring the lordotic curvature of the lumbar (and cervical) spine. Alternatively, the sidewalls 22, 32 may be dimensioned such that the sidewalls comprising the anterior side when the implant is positioned in the disc space have a lesser height than the sidewalls comprising the posterior side, thus restoring the kyphotic curvature of the thoracic spine. The top surfaces 18, 28 and bottom surfaces 20, 30 may be provided in any number of suitable surface contours, including but not limited to generally planar, concave, and/or convex.

The leading element 12 and/or trailing element 16 may also include anti-migration features designed to increase the friction between the implant 10 and the adjacent contacting surfaces of the vertebral bodies. Such anti-migration features may include ridges or teeth 38 provided along the top surfaces 18, 28 and/or bottom surface 20, 30. Additional anti-migration features may also include one or more spike elements 40 disposed at various locations along the implant 10. In one embodiment, the implant 10 includes a total of 4 spike elements 40 extending through the upper surfaces 18, 28 and the lower surfaces 20, 30. Spike elements 40 may be positioned near the "corners" of the implant 10 where the distal end 24 of leading element 12 meets sidewalls 22 and the proximal end 36 of trailing element 16 meets sidewalls 32. The spike elements 40 may be manufactured from any of a variety of suitable materials, including but not limited to a metal, ceramic, and/or polymer material, preferably having radiopaque characteristics. The spike elements 40 may also take any of a variety of suitable shapes, including but not limited to a generally elongated element disposed within the implant 10 such that the ends thereof extend generally perpendicularly from the upper 18, 28 and/or lower surfaces 20, 30. When the spike elements 40 are provided having radiodense characteristics and the leading and trailing elements 12, 16 are manufactured from a radiolucent material (such as, by way of example only, PEEK and/or PEKK), the spike elements 40 will be readily observable under X-ray or fluoroscopy such that a surgeon may track the progress of the implant 10 during implantation and/or the placement of the implant 10 after implantation.

The implant 10 may be configured with one or more fusion apertures 42. Preferably, each of leading element 12 and trailing element 16 include a fusion aperture 42 extending in a vertical fashion through the top surface 18, 28 and bottom surface 20, 30, respectively. The fusion apertures 42 function primarily as an avenue for bony fusion between adjacent vertebrae. The fusion apertures 42 may be provided in any of a variety of suitable shapes, including but not limited to the generally rectangular shape best viewed in FIG. 3, or a generally circular, oblong and/or triangular shape or any combination thereof. The spinal fusion implant 10 may have a plurality of visualization apertures 44 which allow a clinician to make visual observations of the degree of bony fusion un-obscured by the sidewalls 22, 32 of the implant 10 to facilitate further diagnosis and treatment. Preferably, each of leading element 12 and trailing element 16 include at least one visualization aperture 44. Visualization apertures may be provided in any of a variety of suitable shapes, including but not limited to the generally oblong shape best viewed in FIGS. 1-2, or a generally circular, rectangular and/or triangular shape or any combination thereof.

Fusion between the adjacent vertebrae may be facilitated or augmented by introducing or positioning various osteoinductive materials within the fusion apertures 42 and/or adjacent to the spinal fusion implant 10. Such osteoinductive materials may be introduced before, during, or after the insertion of the implant 10, and may include (but are not necessarily limited to) autologous bone harvested from the patient receiving the spinal fusion implant 10, bone allograft, bone xenograft, any number of non-bone implants (e.g. ceramic, metallic, polymer), bone morphogenic protein, and bio-resorbable compositions, including but not limited to any of a variety of poly (D,L-lactide-co-glycolide) based polymers.

The leading element 12 and the trailing element 14 are connected via flexible element 14. Flexible element 14 allows the trailing element 16 to move relative to the leading element 12 (or vice versa). Thus, trailing element 16 (and/or leading element 12) may bend from a neutral position in which the trailing element 16 (and/or leading element 12) is aligned with the longitudinal axis L to a biased position in which the trailing element (and/or the leading element 12) deviates from the longitudinal axis L by and angle $\alpha$. This flexibility allows the implant 10 to adopt various temporary profiles that may be desirable. By way of example, when the operative corridor used to access the disc space is offset or angled relative to the plane of the disc space (due to, for example, one or more anatomical and procedural constraints or considerations) the implant 10 may transition from the offset access trajectory to the disc space in stages (e.g. the leading element 12 may transition before the trailing element 16), thus protecting the vertebral endplates during insertion. The flexible element 14 should thus be flexible enough to allow the trailing element 16 to bend appropriately without effecting the overall integrity and strength of the implant 10.

The flexible element 14 may comprise any number of suitable forms for providing the desired flexibility to the implant 10. By way of example, flexible element 14 may comprise any one or a combination of, but not limited to a spring, a textile body (constructed, for example, via one or more of embroidery, weaving, three-dimensional weaving, knitting, three-dimensional knitting, injection molding, compression molding, cutting woven or knitted fabrics, etc.), and an elastomeric body. According to one embodiment, leading element 12, trailing element 16, and flexible element 14 may be formed of a single component. According to one example of such an embodiment, the entire implant 10 may be formed of polymer material (e.g. PEEK) and a central portion of the component may be machined in a manner that provides the necessary flexibility. Alternatively, leading element 12, trailing element 16, and flexible element 14 may comprise separate components. It will be appreciated that any manner of mechanisms or techniques may be used attach the flexible element 14 to the proximal end 26 of leading element 12 and distal end 34 of trailing element 16, respectively. By way of example only, flexible element 14 may be attached via mechanical fasteners (e.g. snaps, rivets, screws, pins, etc . . . ), chemical bonding, thermal bonding, adhesives, and molding.

As mentioned above, the implant 10 is configured for lateral introduction into the disc space. A lateral approach to the disc space can be highly advantageous over other approaches to the spine. However, the iliac crest of the pelvis generally lies lateral to the L5-S1 disc space making a lateral approach to this spinal level (and thus the advantages that accompany a lateral approach) difficult to achieve in practice. According to one clinical utilization, set forth by way of example only, the implant 10 may be employed to advantageously access and fuse the L5-S1 disc space from a lateral approach, as will now be described. With the patient properly situated on the surgical table (preferably in the lateral decubitus position) an operative corridor is created to the L5-S1 disc space from a skin entry position located superior to L5-S1. By way of example only, the operative corridor may be created using any know tissue distraction and/or tissue retraction systems 46, such as, by way of example only, the tissue distraction and retraction assemblies shown and described in the commonly owned U.S. Pat. No. 7,207,949, the entire contents of which is incorporated by reference into this disclosure as if set forth fully herein. The skin entry position depends upon individual patient anatomy but should be positioned just superior to the iliac crest. The distal end of the tissue distraction/retraction system 46 may then be advanced at an angle towards the L5-S1 disc space, avoiding the iliac crest. Once the distraction/retraction system 46 reaches the L5-S1 disc space, the operative corridor may be expanded by spreading the distraction/retraction system 46 to a final working configuration. Alternatively, the distraction/retraction assembly may be advanced straight to the spine from the skin entry position, and thereafter adjusted to position the distal end of the distraction/retraction system (and thus the operative corridor) adjacent to the L5-S1 disc space.

Figure 4A:
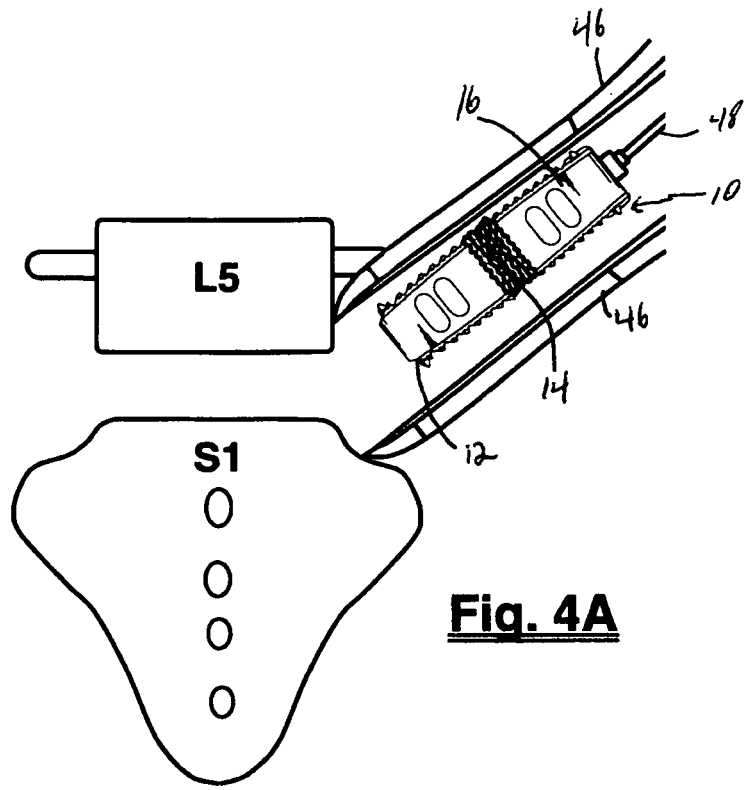
FIG. 4A is a side view of the implant of FIG. 1 being inserted to an intervertebral space through an operative corridor having an axis offset from the plane of the intervertebral space; according to one embodiment of the present invention.

After the creation of the operative corridor, the intervertebral space may be prepared via any number of well known preparation tools, including but not limited to kerrisons, rongeurs, pituitaries, and rasps. According to one embodiment, the preparation tools may utilize distal working ends angularly offset from the longitudinal axis of the tool shafts to facilitate entry into the disc space through the angled operative corridor. After preparation, an insertion instrument 48 is utilized to advance the implant 10 through the operative corridor and into the intervertebral space. As illustrated in FIG. 4A, the implant 10 is preferably advanced through the operative corridor in the neutral position (i.e. with leading element 12 and trailing element 16 aligned with the longitudinal axis L).

Figure 4B:
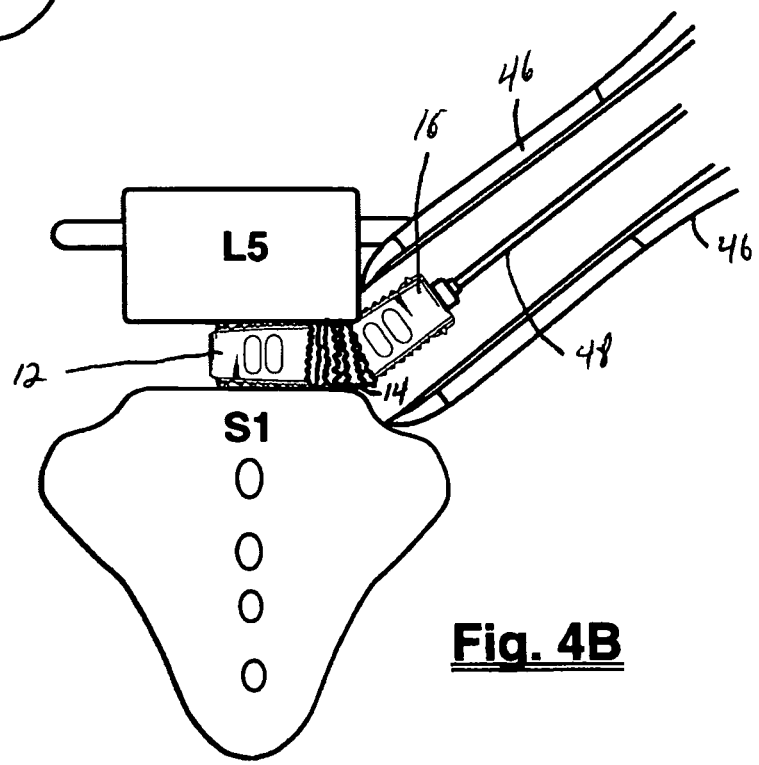
FIG. 4B is a side view of the implant of FIG. 4A with a first element positioned within and aligned with the plane of the disc space and a second element aligned with the axis of the operative corridor prior to being advanced into the disc space, an operative corridor having an axis offset from the plane of the intervertebral space; according to one embodiment of the present invention.
Figure 5:
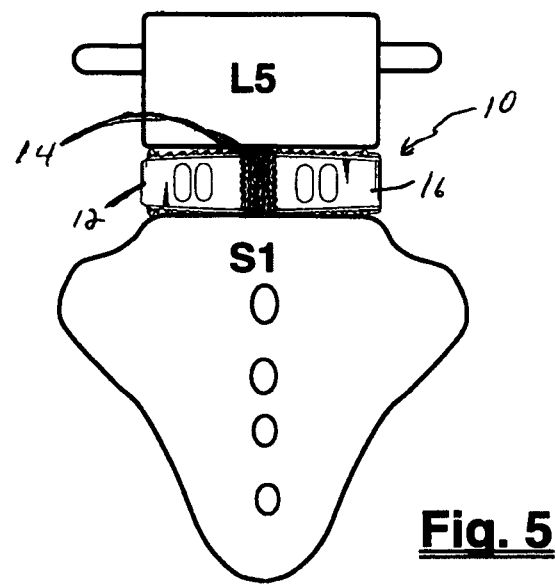
FIG. 5 is a side view of the implant of FIG. 4A completely inserted into an intervertebral space, according to one embodiment of the present invention.

As illustrated in FIG. 4B, the flexible element 14 permits the trailing element 16 to move relative to the leading element 12 as the leading element 12 enters the disc space. In this manner, the longitudinal axis L of the implant is permitted to rotate into alignment with the disc space, despite the small height of the disc space relative to the length of the implant and any space constraints in the operative corridor. The implant 10 may thus be advance into the disc with a reduced risk of gouging or otherwise injuring the vertebral endplates and without requiring a portion of the vertebral body be removed to improve the entry angle into the intervertebral space. The insertion instrument 48 may utilize any number of suitable means for engaging the trailing element 16 of implant 10. To facilitate insertion of the implant 10, the insertion instrument 48 may utilize an angularly offset distal head and/or a flexible shaft. Once the entire implant 10 is inserted into the prepared space and resumes a generally neutral position, the implant 10 is released from the insertion instrument 48, the tissue distraction/retraction system 46 removed, and the operative corridor closed, as depicted in FIG. 5. As previously mentioned, additional materials may be included in the procedure before, during or after the insertion of the spinal fusion implant 10 to aid the natural fusion of the targeted spinal level.

Figure 6:
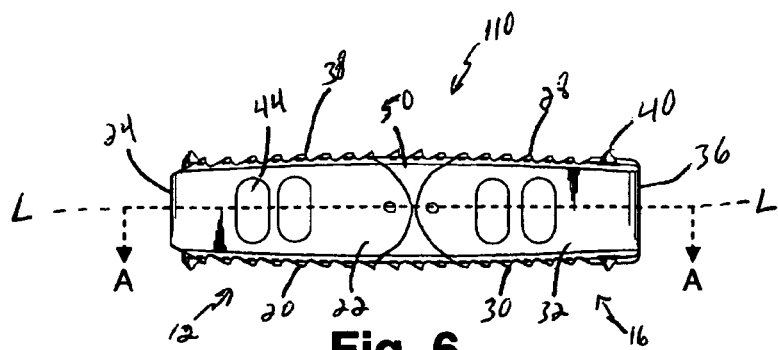
FIG. 6 is a side view of an implant having a first element and a second element movably connected about the longitudinal axis, according to another embodiment of the present invention.
Figures 6A, 7:
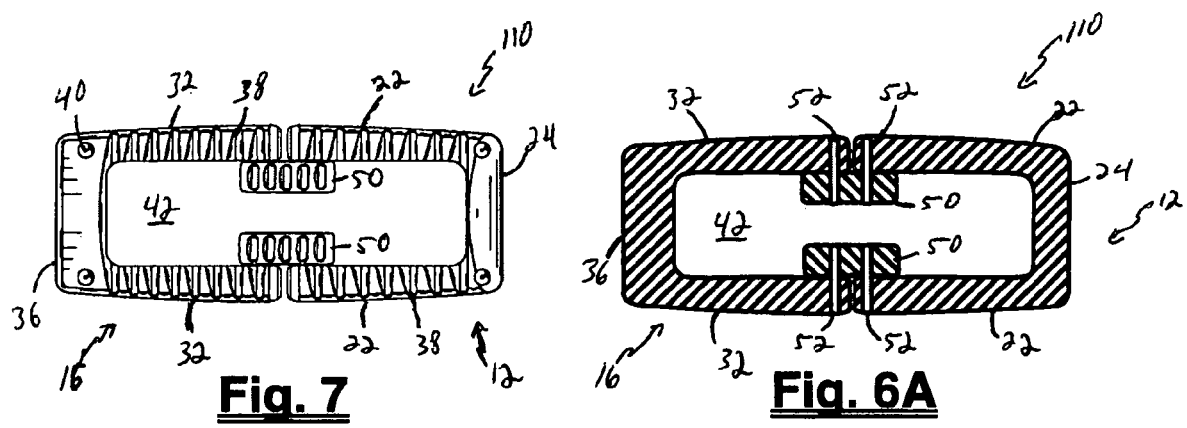
FIG. 6A is a cross-sectional view of the implant of FIG. 6, according to one embodiment of the present invention.
FIG. 7 is a top view of the implant in FIG. 6, according to one embodiment of the present invention.
Figure 8:
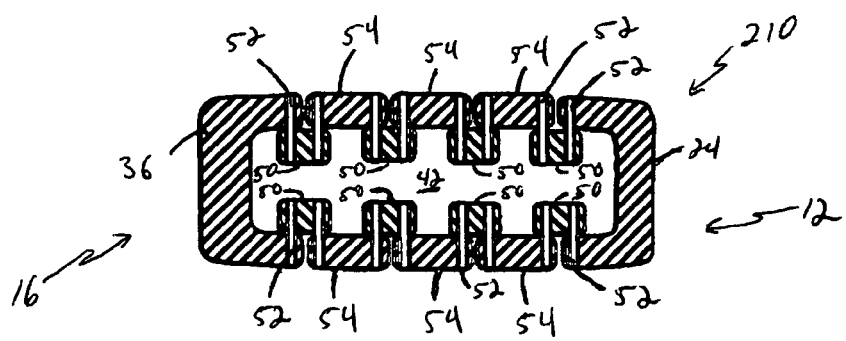
FIG. 8 is a top cross-sectional view of an implant having multiple elements movably connected about the longitudinal axis, according to another embodiment of the present invention.

Alternative example embodiments of implants capable of insertion into the L5-S1 disc space via a lateral surgical approach as described above, are illustrated, by way of example only, in FIGS. 6-13. The alternate embodiments illustrated by way of example, in FIGS. 6-13 are similar to the implant 10 such that repeat discussion of common elements is unnecessary and common elements are numbered accordingly. With reference to FIGS. 6-8, implant 110 includes leading element 12 and trailing element 16. Rather than the flexible member 14 of implant 10, however, the leading element 12 and trailing element 16 are connected by an articulating element 50. The articulating element 50 allows the trailing element 16 to move relative to the leading element 12 (or vice versa). Thus, trailing element 16 (and/or leading element 12) may bend from the neutral position in which the trailing element 16 (and/or leading element 12) is aligned with the longitudinal axis L to a biased position in which the trailing element (and/or the leading element 12) deviates from the longitudinal axis L. Implant 110 may thus adopt various temporary profiles prior to and during insertion into the disc space. The articulating element 50 may be constructed of any suitable biocompatible material, but preferably, comprises the same material as leading element 12 and trailing element 16. As illustrated, one articulating element 50 preferably attaches to an interior surface of both sidewalls 22 and 32 on each side of the implant. By attaching the articulating element 50 to the interior surface of sidewalls 22, 32 the outer dimensions of implant 110 may remain the same or similar to implant 10, however, it will be appreciated that the articulating element 50 may also be attached along the outer surface of sidewalls 22, 32.

As best viewed in FIG. 6A, articulating elements 50 are attached to the leading element 12 and trailing element 16 with fasteners 52. In the illustrated embodiment, fasteners 52 comprise cylindrical pins inserted through both the articulating element 50 and the leading element 12 or trailing element 16. Alternatively, it will be appreciated that fasteners 52 may comprise any suitable connector, such as, for example, a post extending from articulating element 50 into a corresponding aperture on leading element 12 or trailing element 16, or vice versa. FIG. 8 is a cross-sectional view of an implant 210 according to another example embodiment. Implant 210 is identical to implant 110 except that the length of at least one of the leading element 12 and trailing element 16 is shortened and at least one intervening member 54 is situated between leading element 12 and trailing element 16 on each side of the implant 210. As shown, the implant 210 includes three intervening members 54 on each side. For each intervening member 54 added to implant 210 an additional articulating element 50 is also added. Thus, the implant 210 as pictured utilizes four articulating elements 50 on each side of the implant. Decreasing the length of the leading element 12 and trailing element 16 and adding articulating elements 50 and intervening members 54 increases the overall offset angle (of the surgical corridor relative to the plane of the disc space) from which the implant 210 may be safely implanted into the disc space.

Turning now to FIGS. 9-12, an example implant 310 is illustrated. Implant 310 includes a leading element 12, a trailing element 16, and a central element 56. Central element 56 includes a top surface 58, a bottom surface 60, opposing sidewalls 62 (which comprise an anterior side and a posterior side when the implant 310 is positioned in the disc space), a distal end 64, and a proximal end 66. The leading element 12, trailing element 16, and central element 56 are loosely connected in an initial position via at least one wire 68 (and preferably, at least two wires 68 are utilized, as depicted herein) fixed to leading element 12 and passing through central element 56 and trailing element 16, exiting from the proximal end 36 of trailing element 16. The wires 68 may be formed of any suitable material having flexibility enough to allow central element 56 and trailing element 16 to move relative to leading element 12 and each other. Preferably, wire 68 will also provide enough stiffness so that movement between the elements is controlled and not floppy. This controlled movement facilitates initial placement of the leading element 12 within the disc space. By way of example only, the wires 68 may be formed of nitanol or other similar metals. The leading, central, and trailing elements 12, 56, and 16 are further configured to interlock with one another upon final insertion of the implant 310 within the disc space. To accomplish this, central element 56 includes a male snap connector 70 extending from proximal end 66 and a female snap receptacle 72 formed within distal end 64. Extending from proximal end 26, leading element 12 includes a male snap connector 74 complementary to the female snap receptacle 72 of central element 56. Trailing element 16 includes a female snap receptacle 76 within distal end 34.

Figure 9:
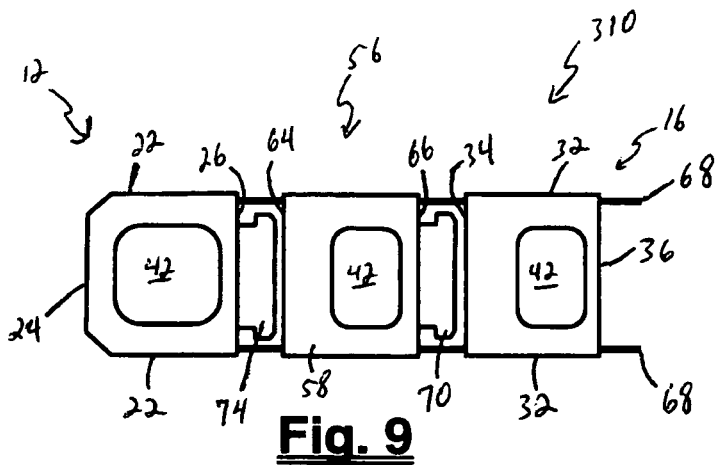
FIG. 9 is a top view of an implant having multiple elements movably connected about the longitudinal axis, according to yet another embodiment of the present invention.
Figure 10:
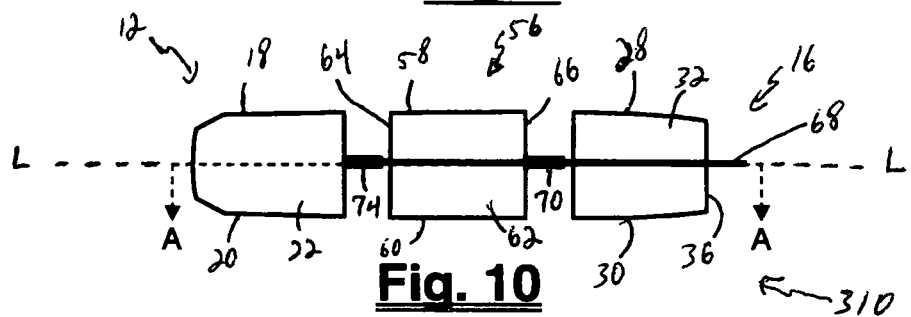
FIG. 10 is a side view of the implant of FIG. 9, according to one embodiment of the present invention.
Figure 10A:
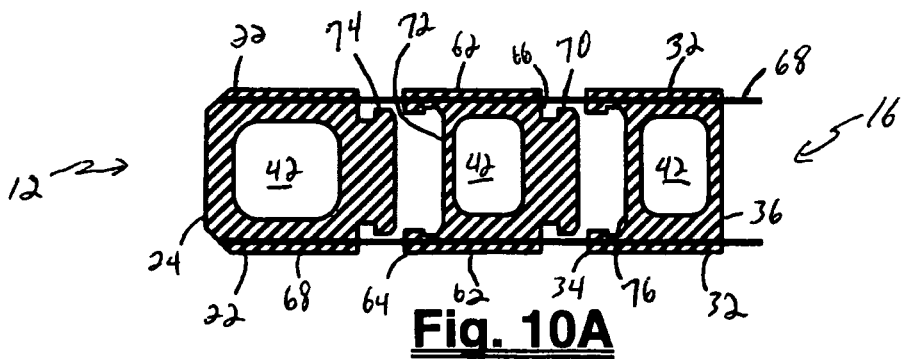
FIG. 10A is a cross-sectional view of the implant of FIG. 9, according to one embodiment of the present invention.
Figure 11:
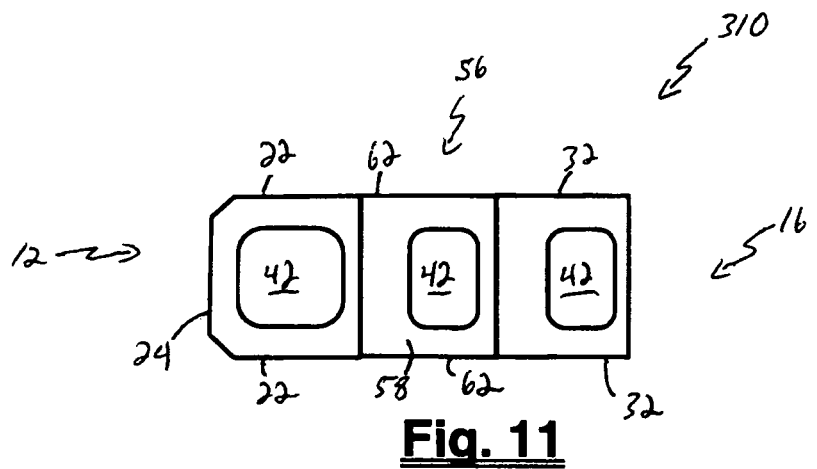
FIG. 11 is a top view of the implant of FIG. 9, wherein the multiple elements are coupled in a locked position, according to one embodiment of the present invention.
Figure 12:
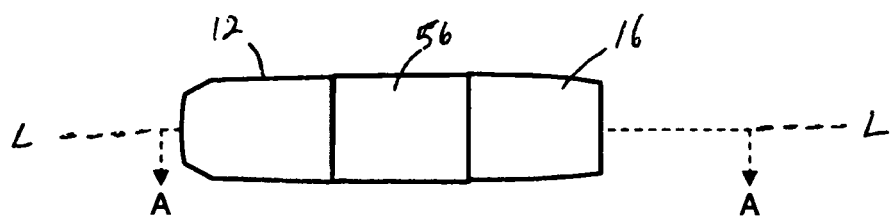
FIG. 12 is a side view of the implant of FIG. 11, according to one embodiment of the present invention.
Figure 11A:
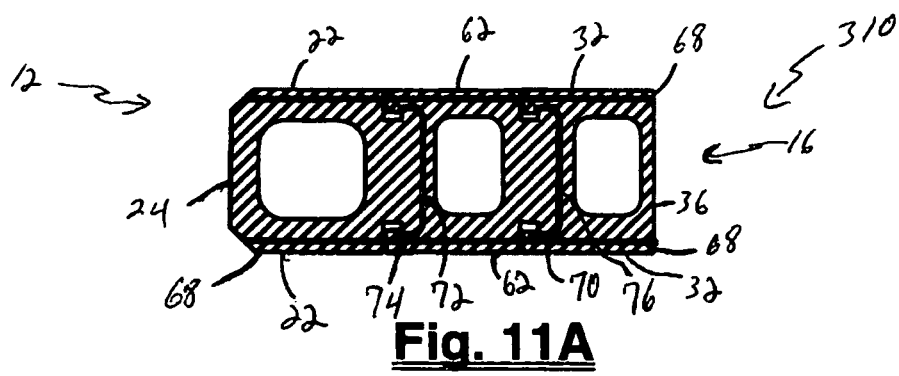
FIG. 11A is a cross-sectional view of the implant of FIG. 11; according to one embodiment of the present invention.

To insert the implant 310, an operative corridor is created as described above. After the leading end 12 is directed to the disc space, the implant advanced all the way into the disc space with the aid of an insertion instrument. Similar to the implants described above, the flexible nature of the wires 68 allows the implant 310 to transition from the offset operative corridor into alignment with the disc space in stages. After the implant is completely advanced into the disc space, the wires 68, which are fixed to leading element 12 may be pulled away from the disc space while pressure is applied to the trailing element 16 in a direction towards the disc space. This combined action draws the leading element and central element together, such that snap connector 74 engages in snap receptacle 72, locking the leading element 12 and central element 56 together. The central element 56 and trailing element 16 will also be drawn together such the snap connector 70 engages in snap receptacle 76, locking central element 56 and trailing element 16 together. Once the implant 310 is locked together within the disc space, the wires 68 extending from trailing element 16 may be removed. This may be accomplished, for example, simply by cutting the exposed portion of wires 68, or any number of other suitable methods. FIGS. 9-10 illustrate the implant 310 prior to locking the leading element 12, central element 56, and trailing element 16 together, while FIGS. 11-12 depict the implant in its final locked position.

Figure 13:
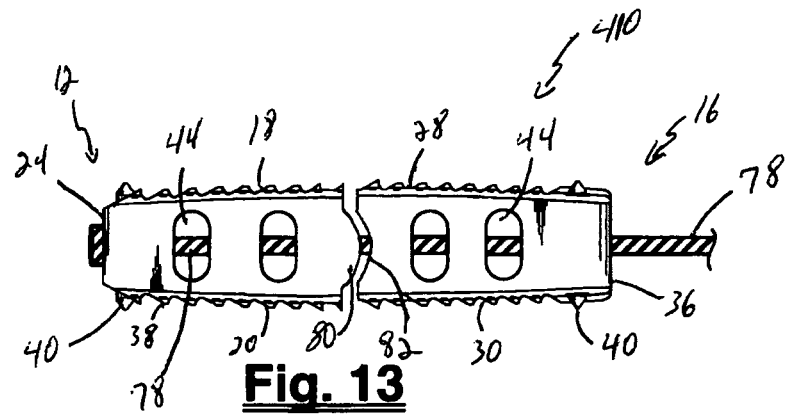
FIG. 13 is a side view of an implant having a first element and a second element movably connected about the longitudinal axis, according to still another embodiment of the present invention.
Figure 14:
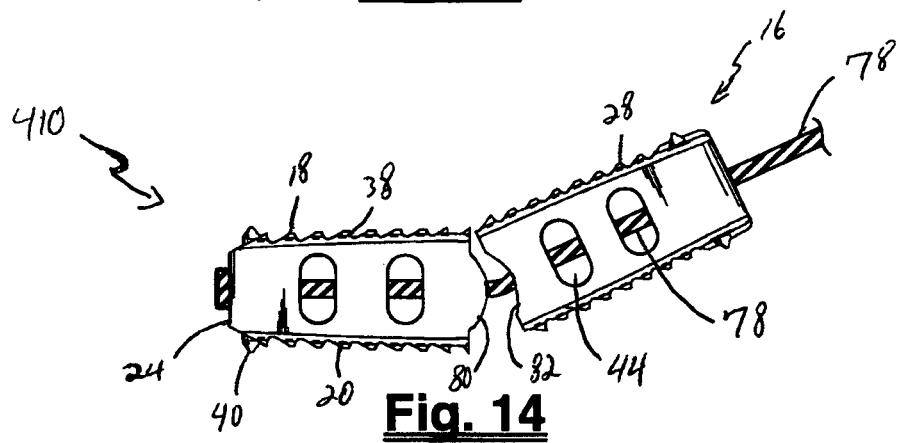
FIG. 14, is a side view of the implant of FIG. 13 wherein an element of the implant is offset relative to the longitudinal axis, according to one embodiment of the present invention.
Figure 15:
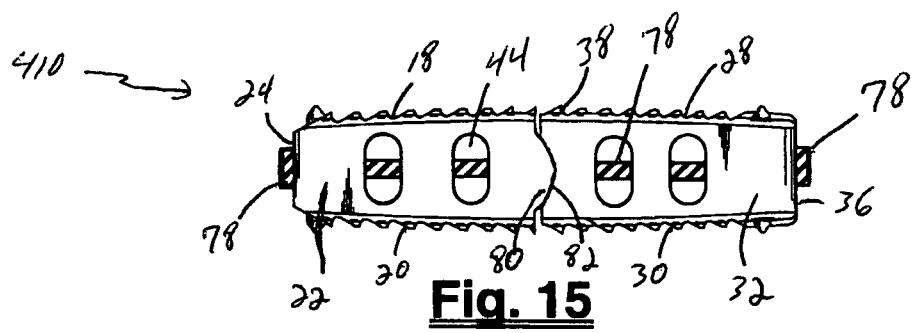
FIG. 15 is a side view of the implant of FIG. 13, wherein first and second elements are aligned with the longitudinal axis of the implant and are drawn tight together after positioning within an intervertebral disc space, according to one embodiment of the present invention.

FIGS. 13-15 depict yet another example embodiment of an implant 410 according to the present invention. Implant 410 comprises leading element 12 and trailing element 16. Leading element 12 and a trailing element 16 are loosely connected by an embroidered tether 78 fixed to leading element 12 and passing through trailing element 16. It will be appreciated that any number of suitable tethers other than the embroidered tether described may be utilized. By way of example only, the tether may be comprised of wire similar to wires 68 described above. The proximal side 26 of leading element 12 and distal side 34 of trailing element 16 are configured with complementary articulating surfaces 80 and 82, respectively. By way of example, articulating surface 80 of leading element 12 comprises a convex extension of sidewalls 22 while the articulating surface 82 of trailing element 16 comprises a concave depression in sidewalls 32. Alternatively, articulating surface 80 could be a concave depression and articulating surface 82 could be a convex extension. The complementary articulating surfaces 80, 82, together with the loose connection provided by tether 78 permit the leading element 12 and trailing element 16 to move relative to each other, and again, like the implants described above, allows implant 410 to transition from alignment in an operative corridor to alignment with the disc space in stages when the disc space is angularly offset form the operative corridor. To deliver implant 410 through the offset operative corridor, the leading end 12 is advanced through the corridor until reaching the disc space. The orientation of the leading element is transitioned into alignment with the disc space and leading element 12 is positioned therein. Initially, the leading implant 410 may be held slightly rigid to facilitate initial positioning of the leading element 12 in the disc space by pulling tether 78 and applying pressure to trailing element 16 with the aid of an insertion instrument. Thereafter, providing slack to the tether 78 allows the trailing element 16 to move relative to the leading element 12 such that the implant can again align with the disc space in stages. After the implant is fully positioned within the disc space, the tether 78 may again be pulled while providing force in the opposite direction with the insertion tool. This draws the leading element 12 and trailing element 16 tightly together and the tether 78 may be tied or otherwise fixed at the proximal end 36 of trailing element 16 to maintain the elements 12, 16 in snug configuration. The excess tether 78 may be removed.

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the invention is to cover all modifications, equivalents, and alternatives falling within the spirit and scope of the invention as defined herein. By way of example only, the description illustrates the use and implantation of implants into the L5-S1 disc space via a lateral approach. It will be appreciated however, that numerous situations may arise where it is desirable to deliver an intervertebral implant through an operative corridor aligned obliquely to the disc space, and the invention is not intended to be limited to the L5-S1 disc space.

What is claimed is:

1. A method of positioning an implant within the intervertebral disc space between a pair of adjacent vertebral endplates, said implant having a longitudinal axis, said disc space having a plane and said plane being generally parallel to said vertebral endplates, said method comprising the steps of:
   a) creating an operative corridor via a lateral approach to said intervertebral disc space, said operative corridor having a longitudinal axis oblique to said disc space plane;
   b) advancing said implant through said operative corridor, wherein said longitudinal axis of said implant is aligned with said operative corridor longitudinal axis;

c) altering the orientation of a first element of said implant such that it is aligned with said disc space plane, while a second element of said implant remains aligned with said operative corridor longitudinal axis;
d) advancing said first element into said disc space,
e) altering the orientation of said second element such that it is aligned with said disc space plane, f) and advancing said second element into said disc space.

2. The method of claim 1, wherein said disc space is L5-S1.

3. The method of claim 1, wherein said operative corridor begins at a skin entry site superior to L5-S1.

4. The method of claim 3, wherein said skin entry site is superior to the iliac crest.

5. The method of claim 4, wherein said operative corridor is created with at least one of a tissue retraction system and a tissue distraction system.

6. The method of claim 1, comprising the additional step of providing said implant with said first element and said second element connected about said longitudinal axis of said implant via a flexible member.

7. The method of 1, comprising the additional step of providing said implant with said first element and said second element connected about said longitudinal axis via an articulating member.

8. The method of 1, comprising the additional step of providing said implant with said first element and said second element connected via at least of a tether and a wire.

* * * * *